United States Patent [19]
Drevillon et al.

[11] Patent Number: 5,485,271
[45] Date of Patent: Jan. 16, 1996

[54] DUAL-MODULATION INTERFEROMETRIC ELLIPSOMETER

[75] Inventors: Bernard Drevillon, Meudon, France; Adolfo C. Biosca, Lleida, Spain

[73] Assignee: Centre National de la Recherche Scientifique, Paris, France

[21] Appl. No.: 418,162

[22] Filed: Apr. 6, 1995

Related U.S. Application Data

[63] Continuation of Ser. No. 2,493, Jan. 6, 1993, abandoned.

[30]  Foreign Application Priority Data

Jan. 7, 1992 [FR] France ................... 92 00090

[51] Int. Cl.⁶ ................................ G01B 9/02
[52] U.S. Cl. ............. 356/345; 356/351; 250/341.1
[58] Field of Search ............. 250/341; 356/351, 356/345, 369, 346

[56] References Cited

U.S. PATENT DOCUMENTS

| | | | |
|---|---|---|---|
| 3,445,833 | 11/1965 | Lins | 356/369 |
| 3,594,085 | 7/1971 | Wilmanns | 356/369 |
| 4,053,232 | 10/1977 | Dill et al. | 356/369 |
| 4,969,200 | 11/1990 | Manns et al. | 356/400 |
| 5,196,903 | 3/1993 | Masutani | 356/346 |

FOREIGN PATENT DOCUMENTS 2602338  2/1988  France .

OTHER PUBLICATIONS

B. Drevillon et al. "Spectroscopic Ellipsometry of Ultrathin Films: From UV to IR", Thin Solid Films, vol. 163 No. 1 Sep. 1988 Lausanne Switzerland pp. 157–166.

F. Ferrieu et al. "Nondestructive Char. of Silicon on Insulator Structures Using Infrared Spectroscope Ellipsometry" Journal of Applied Physics, vol. 68 No. 11 Dec. 1, 1990 New York pp. 5810–5813.

O. Archer et al. "Improvements of Phase Modulated Ellipsometry" Review of Scientific Instr. vol. 60 No. 1 Jan 1989 New York, NY pp. 65–77.

B. Drevillon et al., "Fast Polarization Modulated Ellipsometer Using a microprocessor system for digital Fourier Analysis", *Review of Scientific Instruments*, vol. 53, No. 7, Jul. 1982, New York, New York, pp. 969–977.

Poparization Modulation Fourier Transform Infrared Ellipsometry of Thin Polymer Films; R. T. Graf, F. Eng. J. L. Koenig, and H. Ishida; Applied Spectroscopy; vol. 40, No. 4, 1986; pp. 498–503.

*Primary Examiner*—Samuel A. Turner
*Attorney, Agent, or Firm*—Popham, Haik, Schnobrich & Kaufman, Ltd.

[57] ABSTRACT

The invention relates to an infrared ellipsometer intended to take measurements of a sample (1). An exciter group (3) of the ellipsometer includes a source (101), a Michelson interferometer (103), a polarizer (105), and an optical device (107) to align the source (101) and the sample (1). An analysis group (7) has a polarizer-analyzer (701), a detector (703), and an optical device (705) for aligning the sample (1) and the detector (703). This infrared ellipsometer also incorporates a phase modulator (8). An electronic devices (9) controls the modulator (8) and the Michelson interferometer (103), and receives the signal produced by the detector (703).

10 Claims, 3 Drawing Sheets

DUAL-MODULATION INTERFEROMETRIC ELLIPSOMETER

This is a continuation of U.S. patent application Ser. No. 08/002,493, filed Jan. 6, 1993, now abandoned.

The invention relates to a phase-modulated, Fourier-transform, infrared ellipsometer.

Ellipsometry allows the physical properties of a sample to be determined by optical measurement. The surface of a sample is illuminated by a light beam and the polarization state of the reflected or transmitted beam compared to that of the incident beam. The polarization-vector E is generally represented by its projections $E_s$ and Ep, respectively perpendicular and parallel to the incidence plane; $E_p$ and $E_s$ are complex amplitudes.

BACKGROUND OF THE INVENTION

In the field of ellipsometry, the ratio $(E_p/E_s)^r / (E_p/E_s)^i$ denoting the changes in the polarization state produced by the surface studied, is generally represented in the following form: $tg\psi.exp(i\Delta)=(E_p/E_s)^r/(E_p/E_s)^i$ The object of ellipsometry is therefore to measure the parameters $\psi$ and $\Delta$ for a given surface.

It is thus possible, for example, to study the growth mechanisms of thin films and the formation of interfaces, and even to control a preparation process.

Ellipsometry is a non-destructive, non-interference-generating method of analysis. Measurements can therefore be taken in situ on samples under real conditions of preparation.

Depending on the wavelength domain of the source used (near ultraviolet, visible, near infrared, infrared), different properties of materials can be accessed or different materials scanned.

In the ultraviolet and visible domains, the penetration depth of the beam is often low. Such conditions are ideal for studying surfaces and interfaces, and for real time controls involving cleaning operations. It does not generally give access to the voluminal properties of materials, this being obtainable by measurements taken in the infrared domain.

Infrared is ideal for measuring such properties as vibrational absorption (chemical bonding).

The wavelength domain considered has a determining influence on the measuring devices and instruments used. In fact some components and techniques, known and usable in one wavelength domain, are not transposable or do not give sufficient precision in another.

In the infrared domain, i.e. for wavelengths between approximately 2 and 19 micrometers, different ellipsometers are known.

German patent DE-1572 19 describes a Fourier-transform ellipsometer. This device comprises a Michelson interferometer placed before or after the sample. The sample is placed between a polarizer and an analyzer which are both fixed in orientation during the taking of a measurement. In certain embodiments, a third polarizer is placed between the source and the input polarizer.

French patent FR-2 602 338 describes a phase-modulated ellipsometer comprising a diffraction grating monochromator.

SUMMARY OF THE INVENTION

The object of the present invention is the construction of an infrared ellipsometer with enhanced measuring precision.

A further object of the invention is to propose an infrared ellipsometer that is simple to use and easy to automate.

Another object of the invention is to incorporate the advantages of phase modulation and Fourier-transform spectrometry in the same device.

DETAILED DESCRIPTION OF THE PREFERRED EMBODIMENT

To achieve the above objective invention relates to an infrared ellipsometer intended to measure a sample, and which comprises:

an exciter group, a sample support, an analysis group, electronic means to control the exciter group, receive information from the analysis group and supplies the measurement result.

The exciter group comprises a source, means for polarizing and then modulating the polarized beam, a Michelson interferometer and optical means for aligning the source and the sample.

The analysis group comprises a polarizer-analyzer, a detector and optical means for aligning the sample and the detector.

In accordance with the invention, the means for modulating the polarized beam consist of a phase modulator the electronic means control the phase modulator and Michelson interferometer, and receives the signal produced by the detector.

In a preferred embodiment, the said electronic means comprises a pre-amplifier, an analog-to-digital converter, a Fourier analyzer, a register, a microcomputer.

The pre-amplifier receives at its input the signal sent by the detector and produces an output signal. The signal from the output of the pre-amplifier is sent to the input of the analog-to-digital converter, and a count furnished by the analog-to-digital converter at its output is sent to the input of the Fourier analyzer. The Fourier analyzer also receives a first reference signal sent by the Michelson interferometer, and a second reference signal sent by the phase modulator. The Fourier analyzer then sends values to its output which are representative data of the input signal. These data are received by the register. The microcomputer then stores these data, processes them and provides the measurement result.

The invention also relates to an infrared ellipsometric process for measuring the representative parameters $\psi$ and $\Delta$ of a sample, in which the sample is illuminated by a polarized incident light beam produced by an infrared source, the luminous flux being received and reflected by the sample, analyzed by an analyzer and then measured by a photodetector.

In accordance with the invention, the intensity of the incident luminous flux after passing through a Michelson interferometer comprising a moving mirror whose displacement is x, will be:

$$I(x)=\int I(\theta, t)[(1+\cos 2\pi x)/2]d\theta$$

where $\theta$ is the frequency of the luminous flux at a given moment and t is the time, with $I(\theta, t)$ modulated by the phase modulator at frequency w. It comprises:

a first Fourier-transform processing means which breaks down the signal I ($\theta$, t) into three separate dc components, $S_o$, $S_1$, $S_2$, at frequency w and at frequency 2 w, second processing means giving access to the spectral dependencies $S_o$ ($\theta$), $S_1$ ($\theta$), $S_2$ ($\theta$) through inverse spatial Fourier transform, third processing means producing values $I_o$, $I_s$, $I_c$ from components $S_o$, $S_1$, $S_2$, according to the following formulae, respectively:

$$S_o = I_o + I_c J_o (k\theta),$$

$$S_1 = 2T_1 J_1 (k\theta) I_s$$

$$S_2 = 2T_2 J_2 (k\theta) I_c$$

where $J_o$, $J_s$ and $J_c$, are the Bessel functions of order 0, 1, 2; k is a constant; $T_1$ and $T_2$ are specific constants of the machine, $T_1$, $T_2$ and k are measured by calibration, fourth processing means producing the values $\psi$ and $\Delta$ from $I_o$, $I_s$ and $I_c$ according to trigonometric formulae.

$$I_o = 1 - \cos 2\psi \cos 2A + \cos 2(P-M) \cos 2M(\cos 2A - \cos 2\psi) + \sin 2A \cos \Delta \cos 2(P-M) \sin 2\psi \sin 2M$$

$$I_s = \sin 2(P-M) \sin 2A \sin 2\psi \sin \Delta$$

$$I_c = \sin 2(P-M)\{\sin 2M(\cos 2\psi - \cos 2A) + \sin 2A \cos 2M \sin 2\psi \cos \Delta\}$$

P, M and A being the respective orientations of the polarizer, modulator and analyzer in relation to the incidence plane.

In a particularly preferred embodiment, the frequency of the modulator is between 30 and 60 kHz, the Michelson interferometer scans during an 0.5- to 4-second interval, and the reference laser generates pulses at a frequency in the order of 2 kHz.

A particular embodiment of the invention will now be described in detail with reference to the accompanying drawings, in which:

Figure 1:
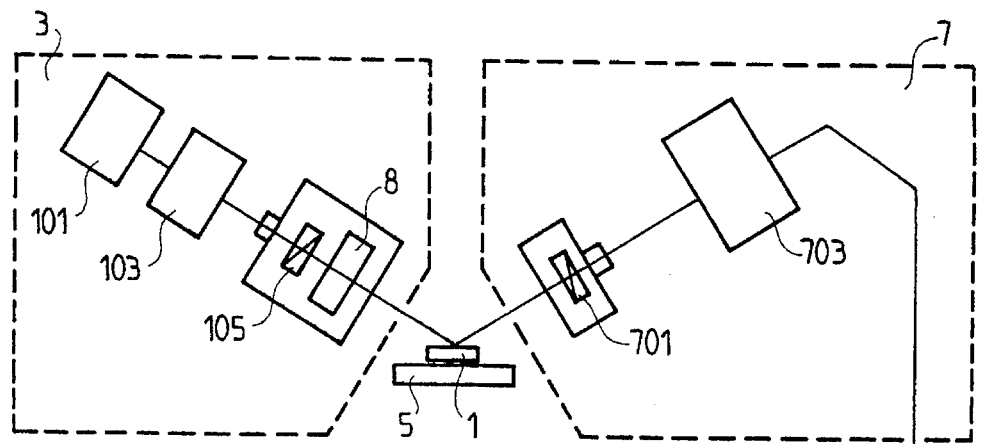
FIG. 1 is a diagrammatic drawing of an ellipsometer in accordance with the invention.
Figure 2:
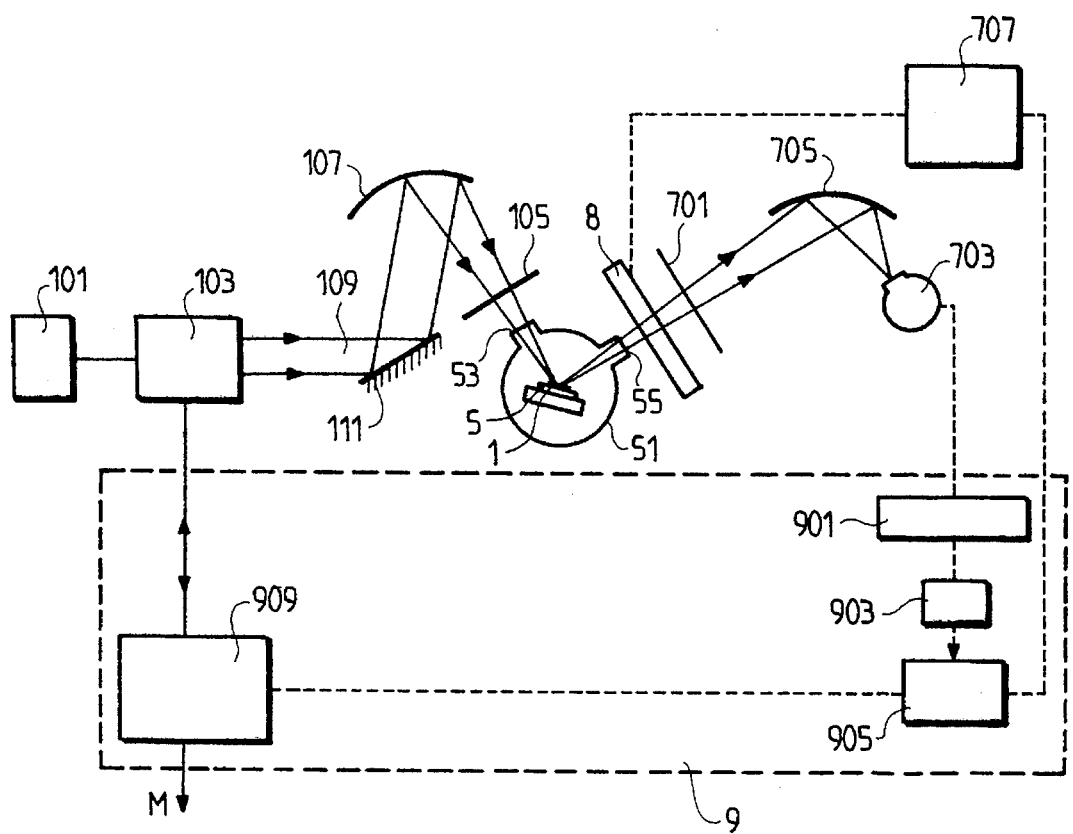
FIG. 2 is a more detailed diagrammatic drawing of the ellipsometer shown in FIG. 1.
Figure 3:
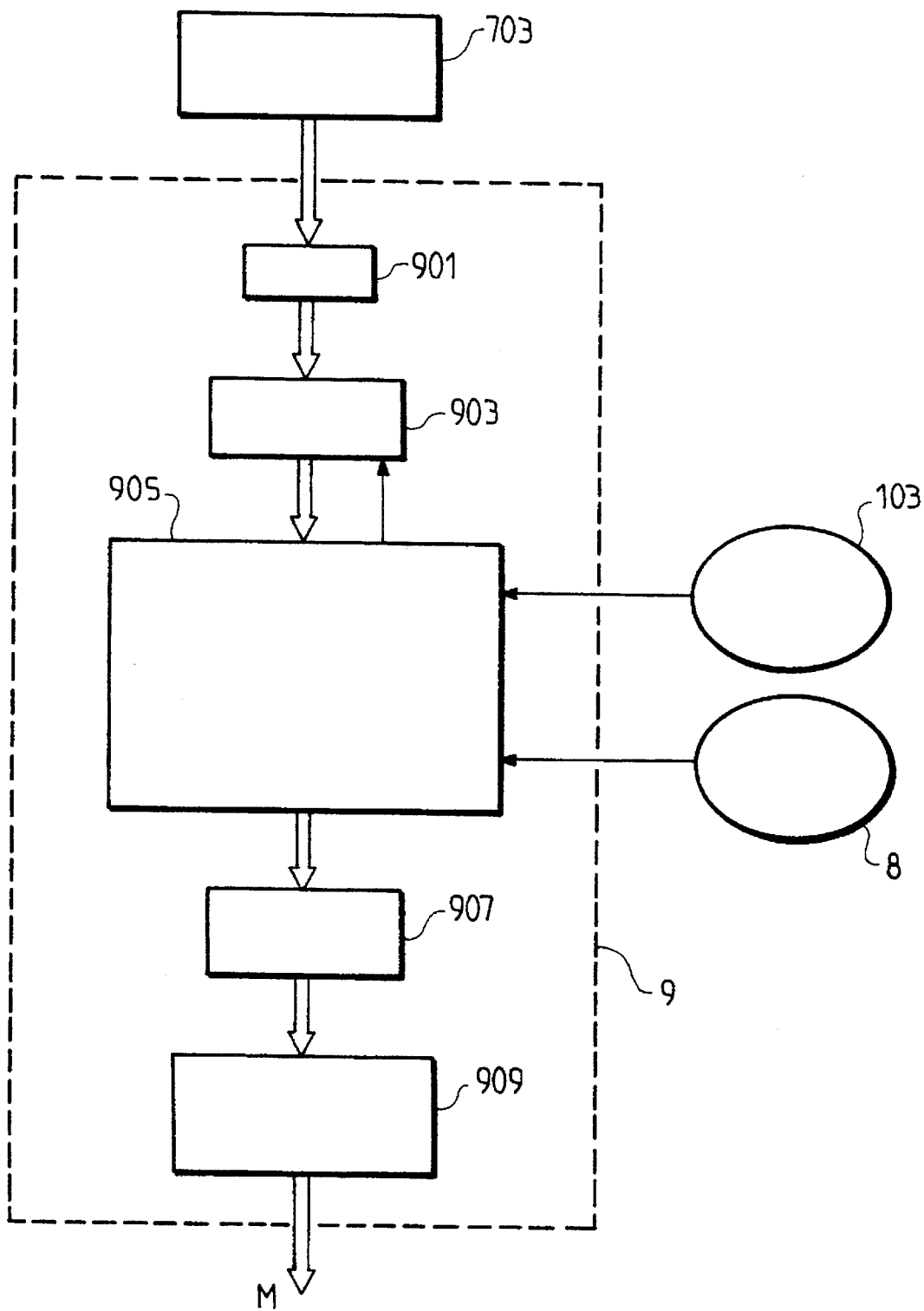
FIG. 3 is a flow chart of the signal processing performed in accordance with the invention.

The infrared ellipsometer is intended for taking a measurement of a sample 1. It comprises an exciter group 3, a sample support 5, an analysis group 7 and electronic means 9.

This ellipsometer is an infrared ellipsometer working in a wavelength range extending from approximately 2 micrometers up to approximately 11 micrometers. The exciter group 3 comprises a Globar type source 101, a Michelson interferometer 103, a polarizer 105, and an optical means 107 for aligning source 101 with sample 1.

In a particularly advantageous embodiment, the Michelson interferometer 103 produces a parallel output beam 109 of circular section, of approximately 38 mm diameter. The optical aligning means 107 represented diagrammatically by a single mirror comprises a parabolic mirror and two spherical mirrors. Flat mirror 111 is used to fold back the beam, thereby reducing the overall dimensions of the device. The beam is therefore focused on a sample whose surface area is approximately 1cm$^2$.

Sample 1 placed on sample support 5 can be inside a reactor or vacuum chamber 51. It is thus possible to take measurements in situ, on condition that the windows 53 and 55 of the vacuum chamber are transparent in the spectral working domain of the ellipsometer and do not modify the polarization state of the transmitted light.

Analysis group 7 comprises a polarizeranalyzer 701, a detector 703, and optical means 705 which align the surface of sample 1 with photodetector 703.

In a preferred embodiment, optical alignment means 705 is composed of a spherical mirror and a parabolic mirror. The surface of excited sample 1 (1 cm$^2$) is aligned with the sensitive surface of detector 703 which measures approximately 1 mm$^2$.

Detector 703 is preferably a photovoltaic liquid-nitrogen-cooled type Hg.Cd.Te detector. Its performance sets the upper limit of the wavelength domain in which the ellipsomter is usable. A limit of 19 micrometers is possible.

The ellipsometer comprises a phase modulator 8, preferably photoelastic, in Zn.Se., which modulates the transmitted luminous flux at a frequency w.

Phase modulator 8 is preferably in exciter group 3. It can, however, be in the receiver group, without noticeably modifying the optical signal form received by photodetector 703.

Electronic means 9 receives, in addition to the electric signal supplied by photodetector 703, a first reference corresponding to the modulator termed high-frequency reference, and various signals originating from Michelson interferometer 103.

These signals, which are lower in frequency than those provided by the modulator, indicate the moments at which spectrum scanning starts and stops, the direction of this scanning comprising a low-frequency reference signal supplied by the reference laser of the Michelson interferometer 103.

The electrical signal supplied by detector 703 is pre-amplified by pre-amplifier 901 and then converted into a digital signal by analog-to-digital converter 903.

One part of the signal supplied by the 16 analog-to-digital converter 903 is used by digital Fourier analyzer 905 which extracts from it the dc component, the component at frequency w and the component at frequency 2 w. To achieve this, component 707 sends it a reference signal at frequency w.

The Fourier analyzer sends its result to register 907 which is preferably a "First In First Out" FIFO register. Microcomputer 909 uses register 907 in such a way as to supply the measured values $\psi$ and $\Delta$ after computation.

To extract the constant components of the signal, at frequency w and at frequency 2 w, the Fourier analyzer 905 receives, first, the high-frequency reference signal at frequency w, and secondly, the low-frequency reference signals originating from Michelson interferometer 103.

The intensity of incident luminous flux 109, after passing through a Michelson interferometer 103 with a moving mirror whose displacement is x, is:

$$I(x) = \int I(\theta, t)[(1 + \cos 2 \pi x)/2] d\theta (P_i)$$

where $\theta$ is the frequency of the luminous flux at a given moment, and t time.

The luminous flux received by detector 703, after said flux has passed via sample 1, is modulated at frequency w by phase modulator 8.

The electric signal supplied in response by photodetector 703 has the same form and can be expressed by approximation, after Fourier decomposition, as follows:

$I(\theta, t) = S_o + S'_1 + S'_2$ where:

$s_0 = I_o + I_c J_o(k\theta)$, $S'_1 = 2T_1 J_1(k\theta) I_s \sin w\, t = S_1 \sin w\, t$ $S'_2 = 2T_1 J_2(k\theta) I_c \cos 2w\, t = S_2 \cos 2wt$ where $J_o$, $J_1$ and $J_2$ are Bessel functions of the 0, 1 2 order; k is a constant; $T_1$ and $T_2$ are specific constants of the ellipsometer.

Fourier analyzer 905 supplies the components $S_o$, $S_1$ and $S_2$ from the signal I($\theta$, t) supplied by photodetector 703.

The ellipsometer is calibrated by positioning the polarizer, phase modulator and analyzer in specific directions.

P, M, A being the respective orientation angles of these three elements in relation to the incidence plane, calibration is performed in the two configurations for which P-M=±45°, A=0°, M=±45°.

This calibration, in conditions where $S_o$, $S_1$, and $S_2$ are independent of the sample, makes it possible to measure parameters $T_2$ and k, aided by an adjustment using the least squares method of the dependency at frequency ($\theta$) of S2/S0.

Measurements taken in orientation conditions of the polarizer, modulator and analyzer different from those mentioned above give new $S_o$, $S_1$, $S_2$ values from which the values of $I_o$, $I_s$ and $I_c$ can be calculated by inversion. $T_1$ is determined in this manner. Thus, it is known that $I_o, I_s$ and $I_c$ are linked to the $\psi$ and $\Delta$ values of the measurement by simple trigonometric formulae.

More precisely, it is known that:

$I_o = 1 - \cos 2\psi \cos 2A + \cos 2(P-M) \cos 2M(\cos 2A - \cos 2\psi) + \sin 2A \cos \Delta \cos 2(P-M) \sin 2\psi \sin 2M$ $I_s = \sin 2(P-M) \sin 2A \sin 2\psi \sin \Delta$ $I_c = \sin 2(P-M) \{\sin 2M(\cos 2\psi - \cos 2A) + \sin 2A \cos 2M \sin 2\psi \cos \Delta\}$ Thus, computer 909 uses the result of the Fourier analysis performed by analyzer 905 to supply the values of measured parameters $\psi$ and $\Delta$ by inverse spatial Fourier transform.

Figure 4:
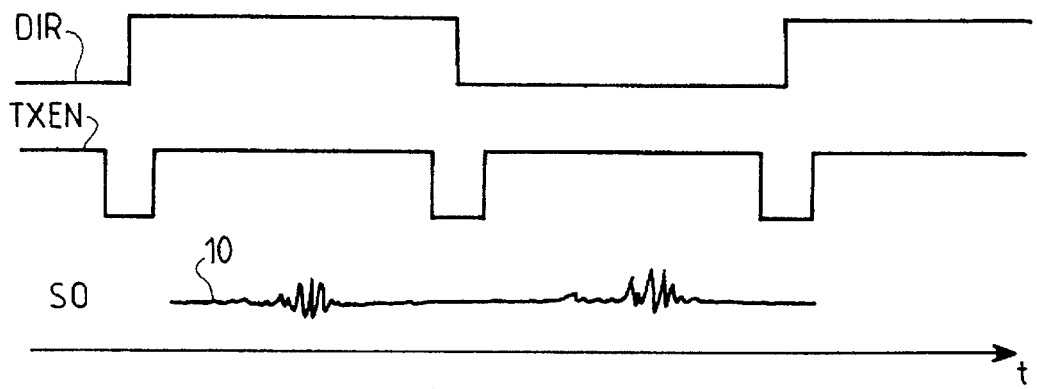
FIGS. 4 and 5 are diagrammatic drawings of the signals supplied by the Michelson interferometer.
Figure 5:
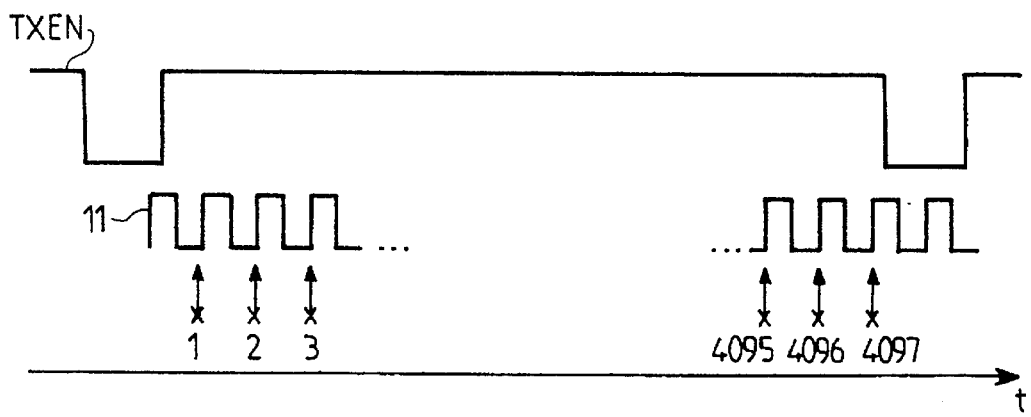
Figure 6:
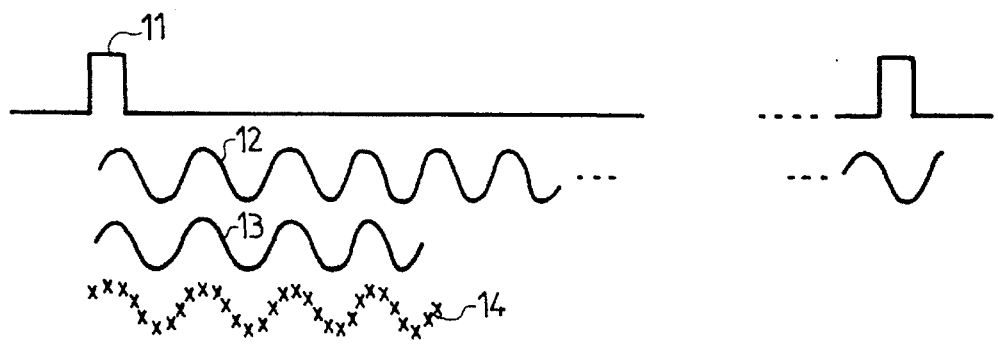
FIG. 6 is a diagrammatic drawing of the data acquisition.

FIG. 4 shows the $S_0$ interference diagram 10 in which the TXEN signal indicates the end and start of scanning of interference diagram 10 by Michelson interferometer 103, and the DIR signal indicates the scanning direction of this interference diagram.

Signal 11 is produced by the reference laser of the Michelson interferometer 103, and provides pulses that are regularly distributed according to the difference in working introduced by the Michelson interferometer.

Preferably, the frequency of this signal is 2,116 kHz, which corresponds to an interferometer mirror scanning speed of 0.66 mm/s.

The frequency w of the high-frequency signal is between 30 and 60 kHz, for example 37 kHz, so that between 10 and 100 periods occur between two reference signals 11 from the laser.

Data acquisition by converter 903 is controlled by digital Fourier analyzer 905. Whenever it receives the reference signal 11 from the laser, it triggers acquisition of one of the points of the interference diagram.

Each point is obtained by integrating four periods of the high-frequency signal 12 (at 37.5 kHz).

For each period of this high frequency signal, the Fourier analyzer 905 takes account of eight conversions of the analog-to-digital converter 903. It is assumed that during the four successive integrating periods 13, variation in the optical paths produced in Michelson interferometer 103 is negligible.

After acquiring thirty-two consecutive points 14, the Fourier analyzer sends the $S_o$, $S_1$, $S_2$ components to register 907.

Computer 909 then processes these values by inverse spatial Fourier transform to provide the ellipsometric values $\psi$ and $\Delta$.

During the acquisition of the thirty-two consecutive points, it must not be forgotten that the reference signals originating respectively from the phase modulator 8 and Michelson interferometer 103 are asynchronous. Alignment is achieved by continuously performing analog-to-digital conversions. Only the digital values produced after the pulse arrives from the reference laser are validated and acquired. An order number is assigned to each stored point which makes it possible to acquire points in phase with the high-frequency modulation (w).

What is claimed is:

1. An infrared ellipsometer for measuring a sample, comprising:
   a) an exciter group including a source, a Michelson interferometer providing a first reference signal, a polarizer, and optical means for aligning said source and the sample, said exciter group generating infrared source energy directed at the sample;
   b) a sample support for supporting the sample;
   c) an analysis group including a polarizer-analyzer, a detector, and optical means for aligning the sample and said detector, said analysis group being aligned for receiving infrared source energy reflected from said sample;
   d) an electro-optical phase modulator, located along a beam path of the infrared source energy, for providing a second reference signal, and modulating at a frequency $\omega$; and
   e) electronic means for controlling said exciter group including the Michelson interferometer, for controlling said electro-optical phase modulator, for receiving signals from said analysis group, and for supplying a measurement result, wherein said electronic means includes:
      1) a pre-amplifier for receiving a signal produced by said detector in said analysis group and for providing a pre-amplifier output signal;
      2) an analog-to-digital converter receiving the pre-amplifier output signal and for providing a digital output signal;
      3) a Fourier analyzer for receiving (A) the digital output signal from said analog-to-digital converter, (B) the first reference signal originating from said Michelson interferometer and (C) the second reference signal originating from said electro-optical phase modulator, for simultaneously extracting the dc component of the digital signal and components of the digital signal at frequencies $\omega$ and $2\omega$, and for producing values which are representative data of the input signal in response to the first reference signal and the second reference signal;

4) a register for receiving the values produced by said Fourier analyzer; and 5) a microcomputer for storing the values produced by said Fourier analyzer, and for generating values of ellipsometer angles of the measurement result by inverse optical Fourier transform.

2. Infrared ellipsometer as claimed in claim 1, wherein:

said Michelson interferometer includes a laser reference;

the laser reference provides a start and end scanning signal (TXEN), a scanning direction signal (DIR) and the first reference signal comprising a number N of equidistant pulses per scan; and said Fourier analyzer uses values of the digital output signal provided by said analog-to-digital converter corresponding to four successive integrating periods of said phase modulator following each pulse of the first reference signal.

3. Infrared ellipsometer as claimed in claim 2, wherein for each working period of said phase modulator, said analog-to-digital converter provides said Fourier analyzer with eight values of the signal.

4. Infrared ellipsometer as claimed in claim 2, wherein on each pulse of the first reference signal, said Fourier analyzer provides said register with coefficients $S_0$, $S_1$ and $S_2$ of the signal.

5. Infrared ellipsometer as claimed in claim 1, wherein said register is a "First in First out" FIFO register.

6. A method of infrared ellipsometric measuring of representative parameters of a sample using an ellipsometer, in which the sample is illuminated by a luminous flux of an incident light beam produced by an infrared source, and in which the luminous flux is reflected by the sample, analyzed by an analyzer and then measured by a photodetector, said method comprising:

a) passing the luminous flux of the incident light beam through a Michelson interferometer having a moving mirror whose displacement is x;

b) generating a first reference signal from the Michelson interferometer;

c) modulating the luminous flux with a phase modulator at a time t;

d) generating a second reference signal from the phase modulator;

e) inputting into a Fourier analyzer an input signal representative of the luminous flux measured by the photodetector, the first reference signal from the Michelson interferometer, and the second reference signal from the phase modulator;

f) simultaneously extracting from the input signal to the Fourier analyzer, dc component $S_0$, and components $S_1$ and $S_2$ at respective frequencies $\omega$ and $2\omega$, based on an intensity I of the incident luminous flux defined as:

$$I(x) = \int I(\theta,t)[(1+\cos 2\pi x)/2]d\theta$$

wherein:

$\theta$ is the frequency of the luminous flux at a given moment;

t is time; and $I(\theta, t)$ is modulated by the phase modulator at frequency $\omega$; and g) generating output signals representative of the values $\psi$ and $\Delta$ based on trigonometric relationships with $I_0$, $I_S$, $I_C$ which are calculated in a microcomputer from the extracted dc components using inverse spatial Fourier transform to determine $S_0$, $S_1$, $S_2$, wherein:

$$S_0 = I_o + I_c J_0(k\theta),$$

$$S_1 = 2T_1 J_1(k\theta) I_s$$

$$S_2 = 2T_2 J_2(k\theta) I_c$$

wherein:

$J_0$, $J_1$ and $J_2$ are Bessel functions of order 0, 1, 2, respectively;

k is a constant;

$T_1$ and $T_2$ are specific constants of the ellipsometer; and $T_1$, $T_2$ and k are measured by calibration.

7. The method of claim 6, wherein the wavelength of a luminous flux emitted by said source is between 1 and 19 micrometers.

8. The method of claim 6, further comprising:

calibrating the ellipsometer by positioning each of the polarizer, phase modulator and analyzer at orientation angles P, M and A, respectively, relative to an incidence of the incident light beam such that $P-M=\pm 45°$, $A=0°$ and $M=\pm 45°$ by adjustment using the least squares method of a spectral dependency ($\theta$) of $S_2/S_0$.

9. The method of claim 6, wherein the frequency of said modulator is between 30 and 60 kHz.

10. The method of claim 6, wherein the scanning time of said Michelson interferometer is any value from 0.5 to 4 seconds.

* * * * *